US006300297B1

(12) United States Patent
Seipel et al.

(10) Patent No.: US 6,300,297 B1
(45) Date of Patent: Oct. 9, 2001

(54) HARD SOAP CONTAINING FATTY ACID POLYGLYCOL ESTER SULPHATES

(75) Inventors: Werner Seipel, Hilden; Bernd Fabry, Korschenbroich; Hermann Hensen, Haan, all of (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/486,138

(22) PCT Filed: Aug. 17, 1998

(86) PCT No.: PCT/EP98/05205

§ 371 Date: May 18, 2000

§ 102(e) Date: May 18, 2000

(87) PCT Pub. No.: WO99/10469

PCT Pub. Date: Mar. 4, 1999

(30) Foreign Application Priority Data

| Aug. 25, 1997 | (DE) | 197 36 906 |
| Sep. 25, 1997 | (DE) | 197 41 911 |
| Feb. 17, 1998 | (DE) | 198 06 494 |

(51) Int. Cl.$^7$ ..................................... A61K 7/50
(52) U.S. Cl. .................. 510/152; 510/153; 510/155; 510/156
(58) Field of Search .................. 510/141, 152, 510/153, 155, 156

(56) References Cited

U.S. PATENT DOCUMENTS

| 1,985,424 | 12/1934 | Piggott . |
| 2,016,962 | 10/1935 | Flint et al. . |
| 2,703,798 | 3/1955 | Schwartz . |
| 4,172,887 | 10/1979 | Vanlerberghe et al. . |
| 5,312,932 | 5/1994 | Behler et al. . |
| 5,322,957 | 6/1994 | Fabry et al. . |
| 5,374,716 | 12/1994 | Biermann et al. . |
| 5,484,531 | 1/1996 | Kuehne et al. . |
| 5,576,425 | 11/1996 | Hill et al. . |

FOREIGN PATENT DOCUMENTS

| 1 089 907 | 9/1960 | (DE) . |
| 1 165 574 | 3/1964 | (DE) . |
| 20 24 051 | 5/1986 | (DE) . |
| 274 049 | 12/1989 | (DE) . |
| 42 04 700 | 8/1993 | (DE) . |
| 195 34 371 | 2/1997 | (DE) . |
| 0 176 330 | 4/1986 | (EP) . |
| 0 189 332 | 7/1986 | (EP) . |
| 0 301 298 | 2/1989 | (EP) . |
| 0 472 320 | 2/1992 | (EP) . |
| 0 508 006 | 10/1992 | (EP) . |
| 0 561 825 | 9/1993 | (EP) . |
| 0 561 999 | 9/1993 | (EP) . |
| 2 252 840 | 12/1978 | (FR) . |
| 962 919 | 7/1964 | (GB) . |
| 1 333 475 | 10/1973 | (GB) . |
| WO89/08444 | 9/1989 | (WO) . |
| WO90/03977 | 4/1990 | (WO) . |
| WO92/06984 | 4/1992 | (WO) . |
| WO94/17172 | 8/1994 | (WO) . |
| WO96/03487 | 2/1996 | (WO) . |
| WO97/40131 | 10/1997 | (WO) . |

OTHER PUBLICATIONS

J.Am.Chem.Soc., 59, No. 10, (Oct., 1982), pp. 442–448.
Ten. Surf. Det., 25, (1988), pp. 8–13.
J.Am.Chem.Soc., 37, (Apr., 1960), pp. 171–175.
J.Am.Chem.Soc., 67, No. 1, (Jan., 1990), pp. 8–14.
Seifen–Ole–Fette–Wachse, 198, (1982), pp. 373–376.
Happi, (Nov., 1986), pp. 70, 72 & 74.
Tens.Surf.Det., 23, (1986), pp. 309–313.
Soap Cosm.Chem.Spec., (Apr., 1990), pp. 46, 47, 50, 114 & 116.
Euro. Cosm., 1, (1994), pp. 14–16.

*Primary Examiner*—Necholus Ogden
(74) *Attorney, Agent, or Firm*—John E. Drach; Steven J. Trzaska

(57) ABSTRACT

A soap composition containing: (a) from 1 to 60% by weight of a fatty acid polyglycol ester sulfate; (b) from 10 to 35% by weight of a fatty acid salt; and (c) remainder, to 100%, water, all weights being based on the total weight of the composition.

14 Claims, No Drawings

HARD SOAP CONTAINING FATTY ACID POLYGLYCOL ESTER SULPHATES

BACKGROUND OF THE INVENTION

This invention relates to new bar soaps which contain anionic surfactants of the fatty acid polyglycol ester sulfate and fatty acid salt type as key components.

Modern bar soaps, more especially toilet soaps, are normally based on mixtures of bovine tallow and coconut oil in a ratio of about 9:1. This fatty mixture is hydrolyzed by addition of sodium hydroxide to the basic soap to which other additives, for example moisturizers, fillers and binders, superfatting agents, dyes and perfumes, etc., are added. Standard toilet soaps contain about 80% fatty acid salts, 10% water and auxiliaries and additives to 100%. The large number of products available to the consumer reflect the keen market interest, but nevertheless make it clear that there is a constant need among consumers for further improved products which are distinguished in particular by improved dermatological compatibility, greater foaming power, greater creaminess, improved refatting, rinse-off behavior, skin feel and the like. By contrast, soap manufacturers are looking for soap formulations which lead, for example, to bars with greater fracture resistance or which allow certain surfactants, for example alkyl sulfates, to be incorporated without difficulty. An overview on this subject can be found, for example, in J. Am. Oil. Chem. Soc. 59, 442 (1982).

So far as the manufacture of bar soaps is concerned, it is possible to look back on a very large number of processes from the prior art. A distinction has to be made in this regard between synthetic "soap-free" soaps, so-called syndets, and in particular combinations of fatty acid salts and synthetic surfactants ("combination bars"). According to EP-A 0 176 330 (Unilever) for example, combination bars are produced by combining fatty acid soaps with salts of isethionic acid. The use of fatty acid isethionates as a synthetic constituent of combination bars is known from EP-A 0 189 332, EP-A 0 472 320 and EP-A 0 508 006 (Unilever).

However, there is a constant need on the market for products with improved properties. In particular, there is a demand for bar soaps which produce a richer and creamier foam than known products and which, in addition, show improved dermatological compatibility. In addition, the soaps should leave the skin with an improved feel and should have a reduced tendency to take up water and to develop cracks. Accordingly, the problem addressed by the present invention was to provide bar soaps that would satisfy the complex requirement profile mentioned above.

DESCRIPTION OF THE INVENTION

The present invention relates to bar soaps containing
(a) 1 to 60, preferably 5 to 15% by weight fatty acid polyglycol ester sulfates,
(b) 10 to 35, preferably 5 to 30% by weight fatty acid salts,
(c) 0 to 40, preferably 1 to 30% by weight anionic, nonionic or amphoteric co-surfactants,
(d) 0 to 10, preferably 1 to 8% by weight fatty acids and
(e) 0 to 40, preferably 1 to 30% by weight water-soluble structurants,
with the proviso that the quantities shown add up to 100% by weight, optionally with water and other typical auxiliaries and additives.

It has surprisingly been found that the bar soaps according to the invention not only produce a particularly stable and creamy foam, they also show improved dermatological compatibility, have an increased water retention capacity on the skin (skin moisture) and a reduced tendency to take up water. The invention includes the observation that the combination of the fatty acid polyglycol ester sulfates with other surfactants, more particularly of the alkyl and/or alkenyl oligoglycoside, fatty add-N-alkyl poly-hydroxyalkyl amide, monoglyceride (ether) sulfate or betaine type or mixtures thereof, leads to bar soaps with further improved properties.

Fatty Acid Polyglycol Ester Sulfates

Fatty acid polyglycol ester sulfates, which form component (a) and preferably correspond to formula (I):

in which $R^1CO$ is a linear or branched, saturated or unsaturated acyl group containing 6 to 22 carbon atoms, x has an average value of 1 to 3 and AO is a $CH_2CH_2O$—, $CH_2CH(CH_3)O$— and/or $CH(CH_3)CH_2O$ group and X is an alkali and/or alkaline earth metal, ammonium, alkylammonium, alkanolammonium or glucammonium, are known anionic surfactants and are produced by sulfation of the corresponding fatty acid polyglycol esters which, in turn, are obtainable by the relevant preparative methods of organic chemistry. To this end, ethylene oxide, propylene oxide or a mixture thereof is added—in random or block distribution - onto the corresponding fatty acids in the presence of an acid as catalyst, but preferably in the presence of bases, for example sodium methylate or calcined hydrotalcite. If a degree of alkoxylation of 1 is required, the intermediate products may also be prepared by esterification of the fatty acids with a corresponding alkylene glycol. The sulfation of the fatty acid polyglycol esters may be carried out in known manner with chlorosulfonic acid or, preferably, gaseous sulfur trioxide, the molar ratio of fatty add glycol ester to sulfating agent being in the range from 1:0.95 to 1:1.2 and preferably in the range from 1:1 to 1:1.1 and the reaction temperature being in the range from 30 to 80° C. and preferably in the range from 50 to 60° C. The fatty acid polyglycol esters may also be undersulfated, i.e. the sulfating agent may be used in far less than the quantity which would be stoichiometrically necessary for a complete reaction. If, for example, the fatty acid polyglycol ester and sulfating agent are used in a molar ratio of 1:0.5 to 1:0.95, mixtures of fatty acid polyglycol ester sulfates and fatty acid polyglycol esters, which are also advantageous for a whole range of applications, are obtained. In order to avoid hydrolysis, it is very important to carry out the neutralization step at a pH value in the range from 5 to 9 and preferably in the range from 7 to 8. Typical examples of suitable starting materials are the addition products of 1 to 3 moles of ethylene oxide and/or propylene oxide, but preferably the addition products of 1 mole of ethylene oxide or 1 mole of propylene oxide with caproic acid, caprylic acid, 2-ethylhexanoic add, capric acid, lauric acid, isotridecanoic acid, myristic acid, palmitic add, palmitoleic acid, stearic acid, isostearic acid, oleic acid, elaidic acid, petroselic acid, linoleic acid, linolenic add, elaeostearic acid, arachic acid, gadoleic acid, behenic acid and erucic acid and technical mixtures thereof, which are then sulfated and neutralized as described above. A preferred embodiment of the invention is characterized by the use of fatty acid polyglycol ester sulfates corresponding to formula (I), in which $R^1CO$ is an acyl group containing 12 to 18 carbon atoms, x has an average value of 1 or 2, AO represents a $CH_2CH_2O$ group and X is sodium or ammonium, such as for example lauric acid+1EO sulfate sodium salt, lauric acid+1EO sulfate ammonium salt, cocofatty add+1EO sulfate sodium salt, cocofatty acid+1EO sulfate ammonium salt, tallow fatty acid+1EO sulfate sodium salt, tallow fatty acid+1EO sulfate ammonium salt and mixtures thereof.

Fatty Acid Salts

Suitable fatty acid salts, which form component (b), are the alkali metal salts of fatty acids containing 6 to 22 and preferably 12 to 18 carbon atoms. Typical examples are the sodium or potassium salts of lauric acid, myristic acid, palmitic acid, stearic acid, behenic acid and technical mixtures thereof such as, for example, cocofatty acid, palm kernel fatty acid, palm oil fatty acid and tallow fatty acid.

Alkyl and/or Alkenyl Oligoglycoside

Alkyl and alkenyl oligoglycosides, which may be present as optional surfactant component (c2), are known nonionic surfactants corresponding to formula (II):

$$R^2O\text{---}[G]_p \tag{II}$$

in which $R^2$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry. EP-A1 0 301 298 and WO 90/03977 are cited as representative of the extensive literature available on the subject. The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (II) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl radical $R^2$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut fatty alcohol by distillation and which may contain less than 6% by weight of $C_{12}$ alcohol as an impurity, and also alkyl oligoglucosides based on technical $C_{9,11}$ oxoalcohols (DP=1 to 3) are preferred. In addition, the alkyl or alkenyl radical $R^2$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut fatty alcohol with a DP of 1 to 3 are preferred.

Fatty Acid-N-alkyl Polyhydroxyalkylamides

Fatty acid-N-alkyl polyhydroxyalkylamides, which may also be present as optional surfactant component (c2), are nonionic surfactants which correspond to formula (III):

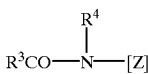

(III)

where $R^3CO$ is an aliphatic acyl group containing 6 to 22 carbon atoms, $R^4$ is an alkyl or hydroxyalkyl group containing 1 to 4 carbon atoms and [Z] is a linear or branched polyhydroxyalkyl group containing 3 to 12 carbon atoms and 3 to 10 hydroxyl groups. The fatty acid-N-alkyl polyhydroxyalkylamides are known compounds which may normally be obtained by reductive amination of a reducing sugar with ammonia, an alkylamine or an alkanolamine and subsequent acylation with a fatty acid, a fatty acid alkyl ester or a fatty acid chloride. Processes for their production are described in U.S. Pat. Nos. 1,985,424, 2,016,962 and 2,703,798 and in International patent application WO 92/06984. An overview of this subject by H. Kelkenberg can be found in Tens. Surf. Det. 25, 8 (1988). The fatty acid N-alkyl polyhydroxyalkylamides are preferably derived from reducing sugars containing 5 or 6 carbon atoms, more particularly from glucose. Accordingly, the preferred fatty acid-N-alkyl polyhydroxyalkylamides are fatty acid-N-alkyl glucamides which correspond to formula (IV):

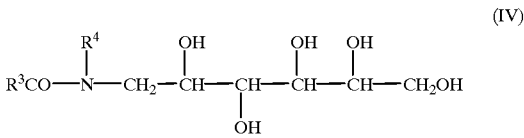

(IV)

Preferred fatty acid-N-alkyl polyhydroxyalkylamides are glucamides corresponding to formula (IV) in which $R^4$ is a methyl group and $R^3CO$ represents the acyl component of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or technical mixtures thereof. Fatty acid-N-alkyl glucamides (IV) obtained by reductive amination of glucose with methylamine and subsequent acylation with lauric acid or $C_{12/14}$ cocofatty acid or a corresponding derivative are particularly preferred. In addition, the polyhydroxyalkylamides may also be derived from maltose and palatinose.

Monoglyceride (Ether) Sulfates

Monoglyceride sulfates and monoglyceride ether sulfates, which may be present as further anionic surfactants (component c3), are known substances which may be obtained by the relevant methods of preparative organic chemistry. They are normally produced from triglycerides which are transesterified to the monoglycerides, optionally after ethoxylation, and then sulfated and neutralized. The partial glycerides may also be reacted with suitable sulfating agents, preferably gaseous sulfur trioxide or chlorosulfonic acid [cf. EP-B1 0561825, EP-B1 0561999 (Henkel)]. If desired, the neutralized products may be subjected to ultrafiltration to reduce the electrolyte content to the required level [DE-A1 4204700 (Henkel)]. Overviews of the chemistry of monoglyceride sulfates have been published, for example, by A. K. Biswas et al. in J. Am. Oil. Chem. Soc. 37, 171 (1960) and by F. U. Ahmed in J. Am. Oil. Chem. Soc. 67, 8 (1990). The monoglyceride (ether) sulfates to be used in accordance with the present invention correspond to formula (V):

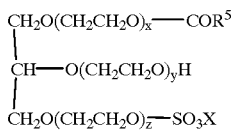

(V)

in which $R^5CO$ is a linear or branched acyl group containing 6 to 22 carbon atoms, x,, y and z together stand for 0 or for numbers of 1 to 30, preferably 2 to 10, and X is an alkali metal or alkaline earth metal. Typical examples of monoglyceride (ether) sulfates suitable for the purposes of the invention are the reaction products of lauric acid monoglyceride, coconut fatty acid monoglyceride, palmitic acid monoglyceride, stearic acid monoglyceride, oleic acid monoglyceride and tallow fatty acid monoglyceride and ethylene oxide adducts thereof with sulfur trioxide or chlorosulfonic acid in the form of their sodium salts. Monoglyceride sulfates corresponding to formula (V), in which $R^5CO$ is a linear acyl group containing 8 to 18 carbon atoms, are preferably used. The monoglyceride (ether) sulfates are preferably used as dried granules or powders which may be obtained, for example, by drying water-containing pastes in a flash dryer.

Betaines

Betaines, which may also be used as representatives of the amphoteric or zwitterionic surfactants, are known substances which are mainly produced by carboxyalkylation, preferably carboxymethylation, of aminic compounds. The starting materials are preferably condensed with halocarboxylic acids or salts thereof, more particularly with sodium chloroacetate, 1 mole of salt being formed per mole of betaine. The addition of unsaturated carboxylic acids, for example acrylic acid, is also possible. Particulars of the nomenclature and, in particular, the distinction between betaines and "genuine" amphoteric surfactants can be found in the article by U. Ploog in Seifen-Öle-Fette-Wachse, 198, 373 (1982). Other reviews of this subject have been published, for example, by A. O'Lennick et al. in HAPPI, Nov. 70 (1986), by S. Holzman et al. in Tens. Surf. Det. 23, 309 (1986), by R. Bibo et al. in Soap Cosm. Chem. Spec., Apr. 46 (1990) and by P. Ellis et al. in Euro Cosm. 1, 14 (1994). Examples of suitable betaines (component c4) are the carboxyalkylation products of secondary and, in particular, tertiary amines corresponding to formula (VI):

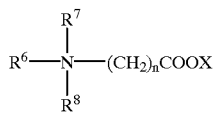

(VI)

in which $R^6$ stands for alkyl and/or alkenyl groups containing 6 to 22 carbon atoms, $R^7$ stands for hydrogen or alkyl groups containing 1 to 4 carbon atoms, $R^8$ stands for alkyl groups containing 1 to 4 carbon atoms, n is a number of 1 to 6 and X is an alkali metal and/or alkaline earth metal or ammonium. Typical examples are the carboxymethylation products of hexyl methyl amine, hexyl dimethyl amine, octyl dimethyl amine, decyl dimethyl amine, dodecyl methyl amine, dodecyl dimethyl amine, dodecyl ethyl methyl amine, $C_{12/14}$ cocoalkyl dimethyl amine, myristyl dimethyl amine, cetyl dimethyl amine, stearyl dimethyl amine, stearyl ethyl methyl amine, oleyl dimethyl amine, $Cl_{6,18}$ tallow alkyl dimethyl amine and technical mixtures thereof. Other suitable betaines are carboxyalkylation products of amidoamines corresponding to formula (VII):

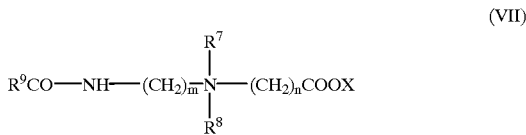

(VII)

in which $R^9CO$ is an aliphatic acyl group containing 6 to 22 carbon atoms and 0 or 1 to 3 double bonds, m is a number of 1 to 3 and $R^7$, $R^8$, n and X are as defined above. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic add, petroselic acid, linoleic acid, linolenic acid, elaeostearic acid, arachic acid, gadoleic acid, behenic acid and erucic acid and technical mixtures thereof, with N,N-dimethyl aminoethyl amine, N,N-dimethyl aminopropyl amine, N,N-diethyl aminoethyl amine and N,N-diethyl aminopropyl amine which are condensed with sodium chloroacetate. It is preferred to use a condensation product of $C_{8/18}$ cocofatty acid-N,N-dimethyl aminopropyl amide with sodium chloroacetate.

Fatty Acids

In the context of the invention, fatty acids which form optional component (d), are aliphatic carboxylic acids corresponding to formula (VIII):

$R^{10}CO—OH$ (VIII)

in which $R^{10}CO$ is an aliphatic, linear or branched acyl group containing 6 to 22 and preferably 12 to 18 carbon atoms and 0 and/or 1, 2 or 3 double bonds. Typical examples are caproic acid, caprylic add, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxo synthesis or in the dimerization of unsaturated fatty adds. Technical fatty acids containing 12 to 18 carbon atoms, for example coconut fatty acid, palm oil fatty acid, palm kernel fatty acid or tallow fatty add, which correspond with the corresponding salts of component (b), are preferred.

Other Auxiliaries and Additives

The bar soaps may contain water-soluble structurants such as, for example, starch, preferably untreated, partly hydrolyzed or acid-degraded wheat or corn starch, or cellulose. In addition, they may contain fine-particle water-insoluble alkali metal alumosilicates as builders, the use of synthetic, crystalline sodium alumosilicates containing bound water, more especially zeolite A, being particularly preferred. Zeolite NaX and mixtures thereof with zeolite NaA may also be used. Suitable zeolites have a calcium binding capacity of 100 to 200 mg CaO/g. NTA and/or EDTA may also be used as liquid builders. Suitable plasticizers are fatty alcohols, fatty acid partial glycerides or wax esters containing 12 to 22 carbon atoms in the fatty components. Suitable emulsifiers are, for example, nonionic surfactants from at least one of the following groups:

(1) products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group;

(2) $C_{12/18}$ fatty acid monoesters and diesters of products of the addition of 1 to 30 moles of ethylene oxide onto glycerol;

(3) glycerol monoesters and diesters and sorbitan monoesters and diesters of saturated and unsaturated fatty acids containing 6 to 22 carbon atoms and ethylene oxide adducts thereof;

(4) adducts of 15 to 60 moles of ethylene oxide with castor oil and/or hydrogenated castor oil;

(5) polyol esters and, in particular, polyglycerol esters such as, for example, polyglycerol polyricinoleate or polyglycerol poly-12-hydroxystearate. Mixtures of compounds from several of these classes are also suitable;

(6) products of the addition of 2 to 15 moles of ethylene oxide onto castor oil and/or hydrogenated castor oil;

(7) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose);

(8) trialkyl phosphates;

(9) wool wax alcohols;

(10) polysiloxane/polyalkyl polyether copolymers and corresponding derivatives;

(11) mixed esters of pentaerythritol, fatty acids, citric acid and fatty alcohol according to DE-PS 1165574 and

(12) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known, commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide with glycerol are known as refatting agents for cosmetic formulations from DE-PS 20 24 051.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers. Aliphatic alcohols (for example ethanol) and polyols (for example glycerol) may also be present. Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, lauryldimonium hydroxypropyl hydrolyzed collagen (Lamequat® L, Grünau GmbH), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz AG), copolymers of acrylic acid with dimethyl diallyl ammonium chloride (Merquat® 550, Chemviron), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3propane, cationic guar gum such as, for example, Jaguar® CBS, Jaguars® C-17, Jaguar® C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/ acrylate copolymers, octylacrylamide/methyl methacrylate/ tert.-butylaminoethyl methacrylate/2-hydroxypropyl methacrylate copolymers, polyvinyl pyrrolidone, vinyl pyrrolidone/vinyl acetate copolymers, vinyl pyrrolidone/ dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature.

Production of the Bar Soaps

The bar soaps according to the invention may be produced by any of the methods normally used for such products, a readily moldable compound which is plastic when hot and hard after cooling being formed by the combination according to the invention of soap and selected quantities of glucosides and/or glucamides and the molded products having a smooth surface. Conventional processes for mixing or homogenizing, kneading, optionally milling, extrusion, optionally pelleting, extrusion, cutting and bar pressing are well-known to the expert and may be used for the production of the bar soaps according to the invention. The production process is preferably carried out at temperatures of 40 to 90°C., the meltable starting materials being introduced into a heatable kneader or mixer and the non-melting components being stirred in. For homogenization, the mixture may then be passed through a sieve before molding. In one preferred embodiment of the invention, components (a) and (d) are used in the water-free granular form obtained after drying in a so-called "flash dryer", cf. the teaching of German patent DE 19534371 C1 (Henkel).

EXAMPLES

Foaming behavior and the creaminess of the foam were determined by the friction foam method and, in the same way as skin feel, were subjectively evaluated by a panel of 6 experienced volunteers on a scale of (+)=satisfactory to +++ (very good). The dermatological compatibility was determined from the total irritation score and is expressed against a standard (C1). The results are set out in Table 1. Preparations 1 to 6 correspond to the invention while the isethionate-based bar soap C1 is intended for comparison.

TABLE 1

Bar soaps - composition (% by weight) and properties

| Composition | 1 | 2 | 3 | 4 | 5 | 6 | C1 |
|---|---|---|---|---|---|---|---|
| Lauric acid + 1EO sulfate sodium salt | 30 | 25 | 25 | 25 | 25 | 25 | 40 |
| Coconut fatty acid sodium salt | 40 | 40 | 35 | 35 | 35 | 40 | — |
| Coconut alkyl oligoglucoside | — | 5 | — | 5 | 5 | — | — |
| Coconut fatty alcohol + 2EO sulfate sodium salt | — | — | 10 | 5 | — | — | — |
| Coconut fatty acid isethionate sodium salt | — | — | — | — | — | — | 30 |
| Betaine based on coconut fatty acid | — | — | — | — | 5 | 5 | — |
| Coconut fatty acid | 8 | 8 | 8 | 8 | 8 | 8 | 8 |
| Wheat starch | 15 | 15 | 15 | 15 | 15 | 15 | 15 |
| Cationic polymer J 400 | — | — | 1 | — | 1 | 1 | — |
| Water | | | | to 100 | | | |
| Foaming behavior | ++ | ++ | +++ | ++ | ++ | ++ | + |
| Creaminess of the foam | ++ | +++ | ++ | ++ | ++ | +++ | ++ |
| Total irritation score | 78 | 72 | 72 | 71 | 72 | 78 | 100 |
| Skin feel | ++ | ++ | ++ | +++ | ++ | +++ | + |

What is claimed is:

1. A soap composition comprising:
   (a) from 1 to 60% by weight of a fatty acid polyglycol ester sulfate;
   (b) from 10 to 35% by weight of a fatty acid salt; and
   (c) remainder, to 100%, water, all weights being based on the total weight of the composition.

2. The composition of claim 1 further comprising from 1 to 30% by weight of a co-surfactant selected from the group consisting of an anionic, a nonionic, an amphoteric, and mixtures thereof.

3. The composition of claim 2 wherein the co-surfactant is a nonionic selected from the group consisting of an alkyl and/or alkenyl oligoglycoside, a fatty acid-N-alkyl polyhydroxyalkyl amide, and mixtures thereof.

4. The composition of claim 1 further comprising from 1 to 8% by weight, based on the weight of the composition, of a fatty acid.

5. The composition of claim 4 wherein the fatty acid is an aliphatic carboxylic acid having from 6 to 22 carbon atoms, and up to 3 double bonds.

6. The composition of claim 1 further comprising from 1 to 30% by weight, based on the weight of the composition, of a water-soluble structurant component.

7. The composition of claim 6 wherein the water-soluble structurant component is starch.

8. A process for making a soap composition comprising:
   (a) providing from 1 to 60% by weight of a fatty acid polyglycol ester sulfate;
   (b) providing from 10 to 35% by weight of a fatty acid salt;
   (c) providing remainder, to 100%, water, all weights being based on the total weight of the composition; and
   (d) mixing (a)–(c) to form the composition.

9. The process of claim 8 wherein the composition further comprises from 1 to 30% by weight of a co-surfactant selected from the group consisting of an anionic, a nonionic, an amphoteric, and mixtures thereof.

10. The process of claim 9 wherein the co-surfactant is a nonionic selected from the group consisting of an alkyl and/or alkenyl oligoglycoside, a fatty acid-N-alkyl polyhydroxyalkyl amide, and mixtures thereof.

11. The process of claim 8 wherein the composition further comprises from 1 to 8% by weight, based on the weight of the composition, of a fatty acid.

12. The process of claim 11 wherein the fatty acid is an aliphatic carboxylic acid having from 6 to 22 carbon atoms, and up to 3 double bonds.

13. The process of claim 8 wherein the composition further comprises from 1 to 30% by weight, based on the weight of the composition, of a water-soluble structurant component.

14. The process of claim 13 wherein the water-soluble structurant component is starch.

* * * * *